(12) United States Patent
Fimognari

(10) Patent No.: US 7,601,832 B2
(45) Date of Patent: Oct. 13, 2009

(54) PROCESS FOR MAKING AZTREONAM

(75) Inventor: Domenico Fimognari, Arese (IT)

(73) Assignee: Sicor, Inc., Irvine, CA (US)

( * ) Notice: Subject to any disclaimer, the term of this patent is extended or adjusted under 35 U.S.C. 154(b) by 417 days.

(21) Appl. No.: 11/431,178

(22) Filed: May 9, 2006

(65) Prior Publication Data

US 2006/0276640 A1  Dec. 7, 2006

Related U.S. Application Data

(60) Provisional application No. 60/679,313, filed on May 9, 2005, provisional application No. 60/681,808, filed on May 17, 2005.

(51) Int. Cl.
*C07D 205/085* (2006.01)

(52) U.S. Cl. .................................. 540/355

(58) Field of Classification Search ............... None
See application file for complete search history.

(56) References Cited

U.S. PATENT DOCUMENTS

| | | | |
|---|---|---|---|
| 4,529,698 A | 7/1985 | Sykes et al. | |
| 4,652,651 A | 3/1987 | Furlenmeier et al. | |
| 4,775,670 A | 10/1988 | Sykes et al. | |
| 4,816,582 A * | 3/1989 | Furlenmeier et al. | 540/355 |
| 4,826,973 A | 5/1989 | Anderson et al. | |
| 4,923,998 A | 5/1990 | Takaya et al. | |
| 4,946,838 A | 8/1990 | Floyd et al. | |
| 5,194,604 A | 3/1993 | Denzel et al. | |
| 5,254,681 A | 10/1993 | Guanti et al. | |
| 2004/0062721 A1 | 4/2004 | Montgomery | |
| 2005/0032775 A1 | 2/2005 | Gyollai et al. | |

FOREIGN PATENT DOCUMENTS

| | | |
|---|---|---|
| EP | 0 070 024 | 1/1983 |
| EP | 0 086 556 | 8/1983 |
| EP | 0 297 580 | 1/1989 |
| EP | 0 464 705 | 1/1992 |
| PL | 165 700 | 8/1993 |
| WO | WO 02/051356 | 7/2002 |
| WO | WO 03/018578 | 3/2003 |
| WO | WO 2004/013133 | 2/2004 |
| WO | WO 2004/052333 | 6/2004 |
| WO | WO 2007/083187 A2 | 7/2007 |
| WO | WO 2007083187 A2 * | 7/2007 |

OTHER PUBLICATIONS

Singh, Org. Proc. Res. Dev., 6 (6), 863 -868, 2002.*
Signh, J. et al. Chemical Abstracts (2002), Accession No. 2002:768758; "Regioselective Activation of Aminothlazole (iminoxyacetic acid)acetic Acid: an Efficient Synthesis of the Monobactam Aztreonam".
Nieschalk, et al. Chemical Abstracts (1996), Accession No. 1996:48264; "Synthesis of Thione Analogs of Monobactams".
Zhu, Y. et al. Chemical Abstracts (1987), Accession No. 1987:101925; "Synthesis of Aztreonam".

* cited by examiner

*Primary Examiner*—Mark L Berch
(74) *Attorney, Agent, or Firm*—Kenyon & Kenyon LLP

(57) ABSTRACT

A simplified process for the one-pot preparation of aztreonam, using azetidine and TAEM as starting materials, without the intermediary separation of t-butyl-aztreonam is provided.

35 Claims, No Drawings

PROCESS FOR MAKING AZTREONAM

RELATED APPLICATION

This application claims benefit of U.S. Provisional Patent Applications Nos. 60/679,313 and 60/681,808, filed May 9, 2005, and May 17, 2005, respectively, the contents of which are incorporated herein in their entirety by reference.

FIELD OF THE INVENTION

The present invention is directed to a process for the synthesis of aztreonam. In particular, the present invention is directed to a "one-pot" process for the synthesis of aztreonam.

BACKGROUND

Aztreonam is a monobactam antibiotic, having the chemical name [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid, and the following structure:

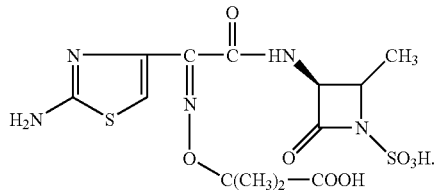

U.S. Pat. No. 4,775,670 discloses a process for acylating a compound of formula:

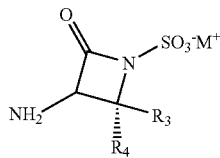

The acylation comprises reacting the compound with a carboxylic acid or the corresponding carboxylic acid halide or carboxylic acid anhydride ($R_1$—OH) in the presence of a carbodiimide such as dicyclohexylcarbodiimide and a substance capable of forming an active ester in situ, such as N-hydroxybenzotriazole. The deprotection in U.S. Pat. No. 4,775,670 is carried out by reaction of the acylation product with trifluoroacetic acid in the presence of anisole under anhydrous conditions. The reagents used in this process are toxic and expensive.

U.S. Pat. No. 4,946,838 discloses an alternative process for making crystalline anhydrous aztreonam and a crystalline anhydrous form of the antibacterial agent. The synthetic path described in this patent is complicated, including, for example, the hydrolysis of a diphenylester protecting group with trifluoroacetic acid in anisole under anhydrous conditions to produce the α-form of aztreonam. The α-form is recrystallized from an anhydrous organic solvent to produce the β-form of aztreonam.

U.S. Pat. No. 5,254,681 discloses a process for preparing aztreonam that comprises acylating azetidine with 2-(2-amino-4-thiazolyl)-2-(Z)-(alkoxyimino)acetic acid in the presence of 1-hydroxy-benzotriazole and dicyclohexylcarbodiimide. The reagents used in this process are toxic and expensive, and their disposal is difficult.

PCT Publication No. WO 2004/013133 discloses a process for preparing aztreonam by hydrolyzing the ester group of [3S-[3α(Z),4β]]-3-[[(2-amino-4-thiazolyl)[(1-t-butoxycarbonyl-1-methylethoxy)imino]acetyl]amino]-4-methyl-2-oxo-1-azetidinesulfonic acid (t-Bu aztreonam) by reacting the ester with an aqueous acid, at elevated temperatures. The application also describes the condensation of azetidine and TAEM with acetonitrile and a base, optionally in the presence of other solvents such as THF, to obtain t-Bu aztreonam.

A further simplification of the process would be desirable. The present invention provides such a simplified process.

SUMMARY

The present invention provides a one-pot process for preparing aztreonam. The process comprises combining azetidine and TAEM in the presence of a $C_1$-$C_3$ tertiary amine and a solvent selected from the group consisting of acetone, 2-butanone, and methyl-isobutyl-ketone (MIBK), to obtain a reaction mixture; adding a first mineral acid to obtain a pH of about 4.5 to about 7.5 to precipitate MBT; isolating the MBT; adding water and a second mineral acid to obtain a pH of less than about 2; heating; and cooling to obtain aztreonam, where the first and second mineral acids may be the same or different.

DETAILED DESCRIPTION

The present invention relates to the preparation of aztreonam in a one-pot process. The process comprises the condensation of azetidine and TAEM in the presence of a $C_1$-$C_3$ tertiary amine and a solvent to obtain t-Bu aztreonam, which is further hydrolyzed to obtain aztreonam. Prior to the hydrolysis step, the by-product MBT, obtained during the condensation of azetidine and TAEM, is isolated from the reaction mixture. The process simplifies the process disclosed in PCT Publication No. WO 2004/013133, due to the reduction of the number of solvents used in the condensation step, and due to the use of a one-pot process. The process is further simplified by substituting the solvent, acetonitrile, with a solvent of acetone, 2-butanone, or methyl-isobutyl-ketone (MIBK), that together with a $C_1$-$C_3$ tertiary amine, enables dissolving both TAEM and aztreonam, and thus, the need for and, thus, the need for excess TAEM, as well as the amount of time required for the reaction to reach completion, is significantly reduced. The removal of the MBT side product simplifies the process, in that the extraction of t-Bu aztreonam in a mixture of ethyl acetate and water is not required.

The one-pot process, which avoids the separation of t-Bu aztreonam, saves time, reduces waste, and improves plant capacity, as that portion of the product that would be lost in the isolation of the t-Bu aztreonam is avoided, and the t-Bu aztreonam is subjected to the next step of the process.

As used herein, the term "t-Bu aztreonam" refers to the compound [3S-[3α(Z),4β]]-3-[[(2-amino-4-thiazolyl)[(1-t-butoxycarbonyl-1-methylethoxy)imino]acetyl]amino]-4-methyl-2-oxo-1-azetidinesulfonic acid.

As used herein, the term "azetidine" refers to a compound having the chemical formula:

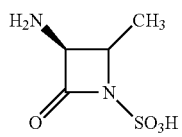

As used herein, the term "MBT", refers to a by-product, having the chemical formula:

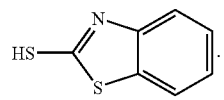

As used herein, the term "TAEM", refers to a compound having the chemical formula:

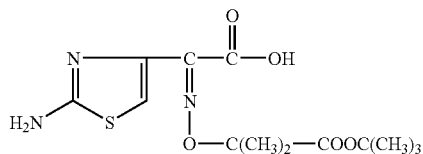

As used herein, the term "$C_1$-$C_3$ tertiary amine" refers to a molecule that contains an atom of nitrogen which is connected to 3 chains, wherein each chain may independently be of $C_1$-$C_3$ alkyl.

The present invention provides a one-pot process for preparing aztreonam. The process comprises combining azetidine and TAEM in the presence of a $C_1$-$C_3$ tertiary amine and a solvent selected from the group consisting of acetone, 2-butanone, and methyl-isobutyl-ketone (MIBK), to obtain a reaction mixture; adding a first mineral acid to obtain a pH of about 4.5 to about 7.5 to precipitate MBT; isolating the MBT; adding water and a second mineral acid to obtain a pH of less than about 2; heating and cooling to obtain aztreonam.

Preferably, the solvent is acetone. Preferably, the $C_1$-$C_3$ tertiary amine is triethylamine. Preferably, the process first comprises mixing the $C_1$-$C_3$ tertiary amine with the solvent at a temperature of about −5° C. to about 30° C., more preferably, at a temperature of about 10° C. to about 15° C. Preferably, the azetidine is added to the mixture of the $C_1$-$C_3$ tertiary amine and the solvent, followed by addition of TAEM. Preferably, the TAEM is added stepwise. Preferably, the azetidine and TAEM are added to the mixture of the $C_1$-$C_3$ tertiary amine and the solvent, while stirring. Preferably, the stirring is for about 30 minutes. Preferably, the reaction mixture containing: a $C_1$-$C_3$ tertiary amine, a solvent, azetidine, and TAEM is maintained for about 4 hours. Preferably, prior to the addition of the first mineral acid, water is added to the reaction mixture. Preferably, after the addition of the water the solvent is removed from the reaction mixture. Preferably, the removal of the solvent is by distillation. Preferably, the distillation is with the water. Preferably, the pH of the reaction mixture, prior to the isolation of MBT, is about 5 to about 6, more preferably, of about 5.5. Preferably, the first and second mineral acids are selected from the group consisting of HCl, $H_2SO_4$, and $H_3PO_4$. More preferably, at least one of the first and second mineral acids is HCl. Preferably, prior to the isolation of MBT, the acidified reaction mixture is further cooled to a temperature of below about 5° C. Preferably, the isolation of MBT is by filtration. Preferably, the pH after the addition of water and a mineral acid is about 1 to about 2, more preferably, the pH is about 1.5. Preferably, the heating is to a temperature of about 50° C. to about 70° C. to obtain a reaction mixture. More preferably, the heating is to a temperature of about 60° C. Preferably, after heating, the process further comprises maintaining for about 4 to about 5 hours, more preferably, for about 5. Preferably, the cooling is to a temperature of about 5° C. to about 0° C. to obtain a precipitate. Preferably, the cooling is for about 4 to about 8 hours, more preferably, for about 5 hours.

Preferably, the process further comprises recovering the aztreonam. Preferably, the recovering comprises filtering, washing with water, slurrying with an anhydrous polar organic solvent, and filtering. After the recovery, a wet aztreonam is obtained. Preferably, the anhydrous polar organic solvent is absolute ethanol or isopropanol methanol.

Preferably, the aztreonam is further crystallized. Washing the aztreonam before crystallization avoids a problematic drying process. The use of an anhydrous polar organic solvent for washing avoids damage to the product during drying, and eliminates any trace of a solvent in the purification process, thus, reducing problems in cleaning the reactor. The crystallization process comprises combining the wet aztreonam with an organic ammonium salt, and adding ethanol, methanol, or isopropanol to obtain a solution. The solution is further acidified with a mineral acid to obtain a pH of about 1 to about 3, cooled to a temperature of about 10° C. to about −10° C., filtered, and dried. Preferably, the ammonium salt is ammonium acetate. Preferably, prior to the addition of ethanol, methanol, or isopropanol, the reaction mixture is cooled to a temperature of about 5° C. to about 0° C. Preferably, the cooled solution is stirred for about 3 hours. Preferably, after adding the second mineral acid and prior to the cooling, the reaction mixture is seeded. Preferably, the seeded reaction mixture is maintained for about 6 hours at a temperature of about 0° C. to about 5° C. Preferably, the acidified reaction mixture is cooled to about 5° C. to about 0° C.

EXAMPLES

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

Example 1

A 50 ml sample of triethylamine is added to a 0.5 l, three necked glass reactor, equipped with condenser and mechanical stirrer with 100 ml of acetone, and cooled to about 10° to about 15° C. Under mixing, 50 g of azetidine is added to the reaction mixture, followed by 43 g of TAEM. Stirring is continued for at least about 30 minutes, until the initially formed color disappears. Two additional 43 g portions of TAEM are then added in the same manner. After the reaction ends, typically after about four hours, water is added to quench the reaction, and the acetone is removed by distillation with the water. The reaction mass is acidified with HCl to a pH of about 5.5, and cooled. Mercaptobenzothiazole (MBT) precipitates, and is separated by filtration.

The pH of the reaction mass containing tertbutylaztreonam is adjusted to about 1.5 with HCl, and diluted with about 400 ml of water. The reaction mass is heated to about 60° C. and maintained at that temperature for about 5 hours. After verifying chromatographically that the deprotection reaction has ended, the reaction mass is cooled slowly over a period of about 5 hours to about 0° to about 5° C. Aztreonam precipitates, and is filtered and washed several times with water. The filter cake is recharged, slurried with 240 ml of absolute ethanol, filtered again, and discharged. About 140 g of wet aztreonam crude is obtained.

Example 2

A 140 g sample of wet aztreonam with 70 g of ammonium acetate is added to a 2 l, three necked glass reactor, equipped with condenser and mechanical stirrer, and is cooled to about 0° to about 5° C. After the addition of 1.2 l of ethanol, the resulting clear solution is mixed for 3 hours at the same temperature. About 15 ml of a 33 percent solution of HCl is added slowly, until a pH of from about 1 to about 3 is reached, and the reaction mass is seeded and maintained for another 6 hours at a temperature of about 0° to about 5° C. The aztreonam is then filtered and dried, providing 60 g of dry aztreonam, an overall yield of about 50 percent.

While it is apparent that the invention disclosed herein is well calculated to fulfill the objects stated above, it will be appreciated that numerous modifications and embodiments may be devised by those skilled in the art. Therefore, it is intended that the appended claims cover all such modifications and embodiments as falling within the true spirit and scope of the present invention.

What is claimed:

1. A one-pot process for preparing aztreonam, comprising combining [3S]3-amino-4-methyl-2-oxo-1-azetidinesulfonic acid and TAEM in the presence of a $C_1$-$C_3$ tertiary amine and a solvent selected from the group consisting of acetone, 2-butanone, and methyl-isobutyl-ketone (MIBK), to obtain a reaction mixture; adding a first mineral acid to obtain a pH of about 4.5 to about 7.5 to precipitate MBT; isolating the MBT; adding water and a second mineral acid, to obtain a pH of less than about 2; heating; and cooling to obtain aztreonam; wherein the first and second mineral acids may be the same or different.

2. The process of claim 1, wherein the solvent is acetone.

3. The process of claim 1, wherein the $C_1$-$C_3$ tertiary amine is triethylamine.

4. The process of claim 1, wherein the $C_1$-$C_3$ tertiary amine and the solvent are first mixed at a temperature of about −5° C. to about 30° C.

5. The process of claim 4, wherein the $C_1$-$C_3$ tertiary amine and the solvent are first mixed at a temperature of about 10° C. to about 15° C.

6. The process of claim 4, wherein the [3S]3-amino-4-methyl-2-oxo-1-azetidinesulfonic acid is added to the mixture of the $C_1$-$C_3$ tertiary amine and the solvent.

7. The process of claim 6, wherein the TAEM is added after the addition [3S]3-amino-4-methyl-2-oxo-1-azetidinesulfonic acid.

8. The process of claim 7, wherein the TAEM is added stepwise.

9. The process of claim 7, wherein the [3S]3-amino-4-methyl-2-oxo-1-azetidinesulfonic acid and TAEM are added to the mixture of the $C_1$-$C_3$ tertiary amine and the solvent, while stirring.

10. The process of claim 1, wherein prior to the addition of the first mineral acid, water is added to the reaction mixture.

11. The process of claim 10, wherein after the addition of the water the solvent is removed from the reaction mixture.

12. The process of claim 11, wherein the removal of the solvent is by distillation.

13. The process of claim 1, wherein the pH prior to the isolation of MBT, is about 5 to about 6.

14. The process of claim 1, wherein the first and second mineral acids are independently selected from the group consisting of HCl, $H_2SO_4$, and $H_3PO_4$.

15. The process of claim 14, wherein at least one of the first and second mineral acids is HCl.

16. The process of claim 1, wherein, prior to the isolation of MBT, the acidified reaction mixture is further cooled to a temperature of below about 5° C.

17. The process of claim 1, wherein the isolation of MBT is by filtration.

18. The process of claim 1, wherein the pH, after the addition of the water and the second mineral acid-is-added, is about 1 to about 2.

19. The process of claim 18, wherein the pH, after the addition of water and a mineral acid, is about 1.5.

20. The process of claim 1, wherein the heating is to a temperature of about 50° C. to about 70° C.

21. The process of claim 20, wherein the heating is to a temperature of about 60° C.

22. The process of claim 1, wherein, after heating, the process further comprises maintaining for about 4 to about 5 hours.

23. The process of claim 22, wherein, after heating, the process further comprises maintaining for about 5 hours.

24. The process of claim 1, wherein the cooling is to a temperature of about 5° C. to about 0° C. to obtain a precipitate.

25. The process of claim 24, wherein the cooling is for about 4 to about 8 hours.

26. The process of claim 1, wherein the process further comprises recovering the aztreonam.

27. The process of claim 26, wherein the recovering comprises filtering, washing with water, slurrying with an anhydrous polar organic solvent, and filtering.

28. The process of claim 27, wherein the anhydrous polar organic solvent is absolute ethanol, isopropanol or methanol.

29. The process of claim 1 or 26, wherein the process further comprises crystallizing the aztreonam by combining the aztreonam with an organic ammonium salt, adding ethanol, methanol, or isopropanol to obtain a solution, acidifying the solution with a mineral acid to obtain a pH of about 1 to about 3, cooling to a temperature of about 10° C. to about −10° C., filtering and drying.

30. The process of claim 29, wherein the ammonium salt is ammonium acetate.

31. The process of claim 29, wherein, prior to the addition of ethanol, methanol, or isopropanol, the reaction mixture is cooled to a temperature of about 5° C. to about 0° C.

32. The process of claim 31, wherein the cooled solution is stirred.

33. The process of claim 29, wherein, after adding the second mineral acid and prior to the cooling, the reaction mixture is seeded.

34. The process of claim 33, wherein the seeded reaction mixture is maintained for about 6 hours at a temperature of about 0° C. to about 5° C.

35. The process of claim 29, wherein the acidified reaction mixture is cooled to about 5° C. to about 0° C.

* * * * *

UNITED STATES PATENT AND TRADEMARK OFFICE
CERTIFICATE OF CORRECTION

PATENT NO. : 7,601,832 B2  Page 1 of 1
APPLICATION NO. : 11/431178
DATED : October 13, 2009
INVENTOR(S) : Domenico Fimognari It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 574 days.

Signed and Sealed this

Fifth Day of October, 2010

David J. Kappos
*Director of the United States Patent and Trademark Office*